United States Patent
Brandt et al.

(10) Patent No.: US 11,090,109 B2
(45) Date of Patent: Aug. 17, 2021

(54) TEMPERATURE-SENSING ELECTRICALLY-CONDUCTIVE TISSUE-CONTACTING PLATE CONFIGURED FOR USE IN AN ELECTROSURGICAL JAW MEMBER, ELECTROSURGICAL SYSTEM INCLUDING SAME, AND METHODS OF CONTROLLING VESSEL SEALING USING SAME

(71) Applicant: COVIDIEN LP, Mansfield, MA (US)

(72) Inventors: Kim V. Brandt, Loveland, CO (US); Allan G. Aquino, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 427 days.

(21) Appl. No.: 14/538,402

(22) Filed: Nov. 11, 2014

(65) Prior Publication Data

US 2015/0223868 A1    Aug. 13, 2015

Related U.S. Application Data

(60) Provisional application No. 61/938,232, filed on Feb. 11, 2014.

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1206* (2013.01); *A61B 18/1442* (2013.01);
(Continued)

(58) Field of Classification Search
CPC ............ A61B 18/1442; A61B 18/1445; A61B 2018/00797
See application file for complete search history.

(56) References Cited

U.S. PATENT DOCUMENTS

D249,549 S    9/1978 Pike
D263,020 S    2/1982 Rau, III
(Continued)

FOREIGN PATENT DOCUMENTS

CN    201299462        9/2009
DE    2415263 A1    10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Michael F Peffley
*Assistant Examiner* — Bo Ouyang
(74) *Attorney, Agent, or Firm* — Carter, DeLuca & Farrell LLP

(57) ABSTRACT

An electrosurgical system includes an electrosurgical instrument, an electrosurgical power generating source, and a controller. The electrosurgical instrument includes a shaft extending from a housing. The shaft includes a distal end configured to support an end-effector assembly. The end-effector assembly includes opposing jaw members movably mounted with respect to one another and moveable from a first position in spaced relation relative to one another to at least one subsequent position wherein the jaw members cooperate to grasp tissue therebetween. At least one of the jaw members includes a temperature-sensing electrically-conductive tissue-contacting plate defining a bottom surface. One or more temperature sensors are coupled to the bottom surface. The controller is configured to control one or more operating parameters associated with the electrosurgical power generating source based on one or more signals
(Continued)

indicative of a tissue impedance value and indicative of a temperature sensed by the one or more temperature sensors.

12 Claims, 10 Drawing Sheets

(52) U.S. Cl.
CPC .............. *A61B 2018/0016* (2013.01); *A61B 2018/0063* (2013.01); *A61B 2018/0072* (2013.01); *A61B 2018/00404* (2013.01); *A61B 2018/00648* (2013.01); *A61B 2018/00702* (2013.01); *A61B 2018/00714* (2013.01); *A61B 2018/00726* (2013.01); *A61B 2018/00755* (2013.01); *A61B 2018/00767* (2013.01); *A61B 2018/00791* (2013.01); *A61B 2018/00797* (2013.01); *A61B 2018/00875* (2013.01); *A61B 2018/1455* (2013.01)

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,417,686 A * | 5/1995 | Peterson | A61B 18/00 606/25 |
| 5,582,609 A * | 12/1996 | Swanson | A61L 31/10 606/33 |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,892,228 B2 * | 2/2011 | Landis | A61B 17/2812 606/41 |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 2002/0091382 A1 | 7/2002 | Hooven | |
| 2002/0120267 A1 * | 8/2002 | Phan | A61B 18/1445 606/51 |
| 2003/0158549 A1 * | 8/2003 | Swanson | A61B 18/1445 606/41 |
| 2006/0217706 A1 * | 9/2006 | Lau | A61B 17/29 606/45 |
| 2007/0203481 A1 * | 8/2007 | Gregg | A61B 18/1233 606/34 |
| 2010/0076432 A1 | 3/2010 | Horner | |
| 2011/0319881 A1 * | 12/2011 | Johnston | A61B 18/1206 606/33 |
| 2013/0103035 A1 | 4/2013 | Horner et al. | |
| 2013/0245619 A1 * | 9/2013 | Yasunaga | A61B 18/085 606/31 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 2272453 A1 | 1/2011 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |

(56) References Cited

FOREIGN PATENT DOCUMENTS

| | | |
|---|---|---|
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002. . . .
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.

(56) References Cited

OTHER PUBLICATIONS

Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C. . . .
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C. . . .
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
U.S. Appl. No. 13/731,674, filed Dec. 31, 2012; inventor: Siebrecht.
U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Extended European Search Report dated Jul. 3, 2015, issued in EP Application No. 14200057.

* cited by examiner

TEMPERATURE-SENSING ELECTRICALLY-CONDUCTIVE TISSUE-CONTACTING PLATE CONFIGURED FOR USE IN AN ELECTROSURGICAL JAW MEMBER, ELECTROSURGICAL SYSTEM INCLUDING SAME, AND METHODS OF CONTROLLING VESSEL SEALING USING SAME

CROSS REFERENCE TO RELATED APPLICATION

The present application claims the benefit of and priority to U.S. Provisional Application Ser. No. 61/938,232, filed on Feb. 11, 2014, the entire contents of which are incorporated herein by reference.

BACKGROUND

1. Technical Field

The present disclosure relates to electrosurgical instruments. More particularly, the present disclosure relates to temperature-sensing electrically-conductive tissue-contacting plates configured for use in electrosurgical jaw members, electrosurgical systems including the same, and methods of controlling vessel sealing using the same.

2. Discussion of Related Art

Electrosurgical instruments, such as electrosurgical forceps, are well known in the medical arts. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end-effector) adapted to transmit energy to a tissue site during electrosurgical procedures. Electrosurgery is typically performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode.

In bipolar electrosurgery, both the active electrode and return electrode functions are performed at the site of surgery. Bipolar electrosurgical devices include two electrodes that are located in proximity to one another for the application of current between their respective surfaces. Bipolar electrosurgical current travels from one electrode, through the intervening tissue to the other electrode to complete the electrical circuit. Bipolar instruments generally include end-effectors, such as graspers, cutters, forceps, dissectors and the like.

Bipolar electrosurgical forceps utilize two generally opposing electrodes that are operably associated with the inner opposing surfaces of the end-effectors and that are both electrically coupled to an electrosurgical generator. In bipolar forceps, the end-effector assembly generally includes opposing jaw members pivotably mounted with respect to one another. In a bipolar configuration, only the tissue grasped between the jaw members is included in the electrical circuit. Because the return function is performed by one jaw member of the forceps, no patient return electrode is needed.

A variety of types of end-effector assemblies have been employed for various types of electrosurgery using a variety of types of monopolar and bipolar electrosurgical instruments. Jaw member components of end-effector assemblies for use in electrosurgical instruments are required to meet specific tolerance requirements for proper jaw alignment and other closely-toleranced features. Gap tolerances and/or surface parallelism and flatness tolerances are parameters that, if properly controlled, can contribute to a consistent and effective tissue seal. Thermal resistance, strength and rigidity of surgical jaw members also play a role in determining the reliability and effectiveness of electrosurgical instruments.

By utilizing an electrosurgical forceps, a surgeon can cauterize, coagulate, desiccate and/or seal tissue and/or simply reduce or slow bleeding by controlling the intensity, frequency and duration of the electrosurgical energy applied through the jaw members to the tissue. During the sealing process, mechanical factors such as the pressure applied to the vessel or tissue between opposing jaw members and the gap distance between the electrically-conductive tissue-contacting surfaces (electrodes) of the jaw members play a role in determining the resulting thickness of the sealed tissue and effectiveness of the seal. Accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. A variety of instruments have been developed that utilize technology to form a vessel seal utilizing a combination of pressure, gap distance between opposing surfaces and electrical control to effectively seal tissue or vessels.

Methods and systems have been developed for controlling an output of a generator, such as a radio-frequency (RF) electrosurgical generator, based on sensor signals indicative of impedance changes at a surgical site. In some systems employing changes in impedance to control the amount of electrosurgical energy applied to tissue, when the sensor signal meets a predetermined level based on a control algorithm, the system provides an end tone that indicates to the surgeon that a procedure, such as a vessel-sealing procedure, is complete. In generators employing an impedance-based control algorithm, impedance is a proxy for temperature, and there are cases where an end tone may be given when no tissue sealing has occurred because the impedance proxy was incorrect.

SUMMARY

A continuing need exists for methods and systems for controlling one or more operating parameters of an electrosurgical power generating source based on one or more signals indicative of a temperature sensed by one or more temperature sensors. A continuing need exists for temperature-sensing devices that can be readily integrated into the manufacturing process for electrosurgical jaw members.

According to an aspect of the present disclosure, an electrosurgical system is provided. The electrosurgical system includes an electrosurgical instrument, an electrosurgical power generating source, and a controller. The electrosurgical instrument includes a housing and a shaft extending from the housing. The shaft includes a distal end configured to support an end-effector assembly. The end-effector assembly includes opposing jaw members movably mounted with respect to one another At least one of the jaw members includes a temperature-sensing electrically-conductive tissue-contacting plate defining a tissue-contacting surface and a bottom surface. One or more temperature sensors are coupled to the bottom surface. The jaw members are moveable from a first position in spaced relation relative to one another to at least one subsequent position wherein the jaw members cooperate to grasp tissue therebetween. The electrosurgical system also includes an electrosurgical power generating source and a controller operably coupled to the electrosurgical power generating source. The controller is configured to control one or more operating parameters associated with the electrosurgical power generating source based on one or more signals indicative of a tissue impedance value and indicative of a temperature sensed by the one or more temperature sensors.

According to another aspect of the present disclosure a method of controlling vessel sealing is provided including the initial step of providing an electrosurgical instrument having an end-effector assembly including opposing jaw members movably mounted with respect to one another, each one of the jaw members including a temperature-sensing electrically-conductive tissue-contacting plate having a tissue-contacting surface and a bottom surface. The method also includes the steps of moving at least one jaw member relative to the other jaw member to grasp tissue between the tissue-contacting surface of each one of the temperature-sensing electrically-conductive tissue-contacting plates, transmitting energy from an electrosurgical power generating source to at least one of the jaw members, and controlling one or more operating parameters associated with the electrosurgical power generating source based on one or more signals indicative of a temperature sensed by one or more temperature sensors.

According to another aspect of the present disclosure a method of controlling vessel sealing is provided. The method includes the initial step of providing an electrosurgical instrument having an end-effector assembly including opposing jaw members movably mounted with respect to one another. At least one of the jaw members includes a temperature-sensing electrically-conductive tissue-contacting plate having a tissue-contacting surface and a bottom surface. The method also includes the steps of positioning the jaw members to energize tissue, transmitting energy from an electrosurgical power generating source to the at least one of the jaw members, transmitting one or more signals indicative of a tissue impedance value and a tissue temperature value to a controller operably associated with the electrosurgical power generating source, and controlling one or more operating parameters associated with the electrosurgical power generating source based on the one or more signals indicative of the tissue impedance value and the tissue temperature value sensed by the one or more temperature sensors.

BRIEF DESCRIPTION OF THE DRAWINGS

Objects and features of the presently-disclosed temperature-sensing electrically-conductive tissue-contacting plate configured for use in an electrosurgical jaw member, electrosurgical systems including the same, and methods of controlling vessel sealing using the same will become apparent to those of ordinary skill in the art when descriptions of various embodiments thereof are read with reference to the accompanying drawings, of which.

DETAILED DESCRIPTION

Figure 1:
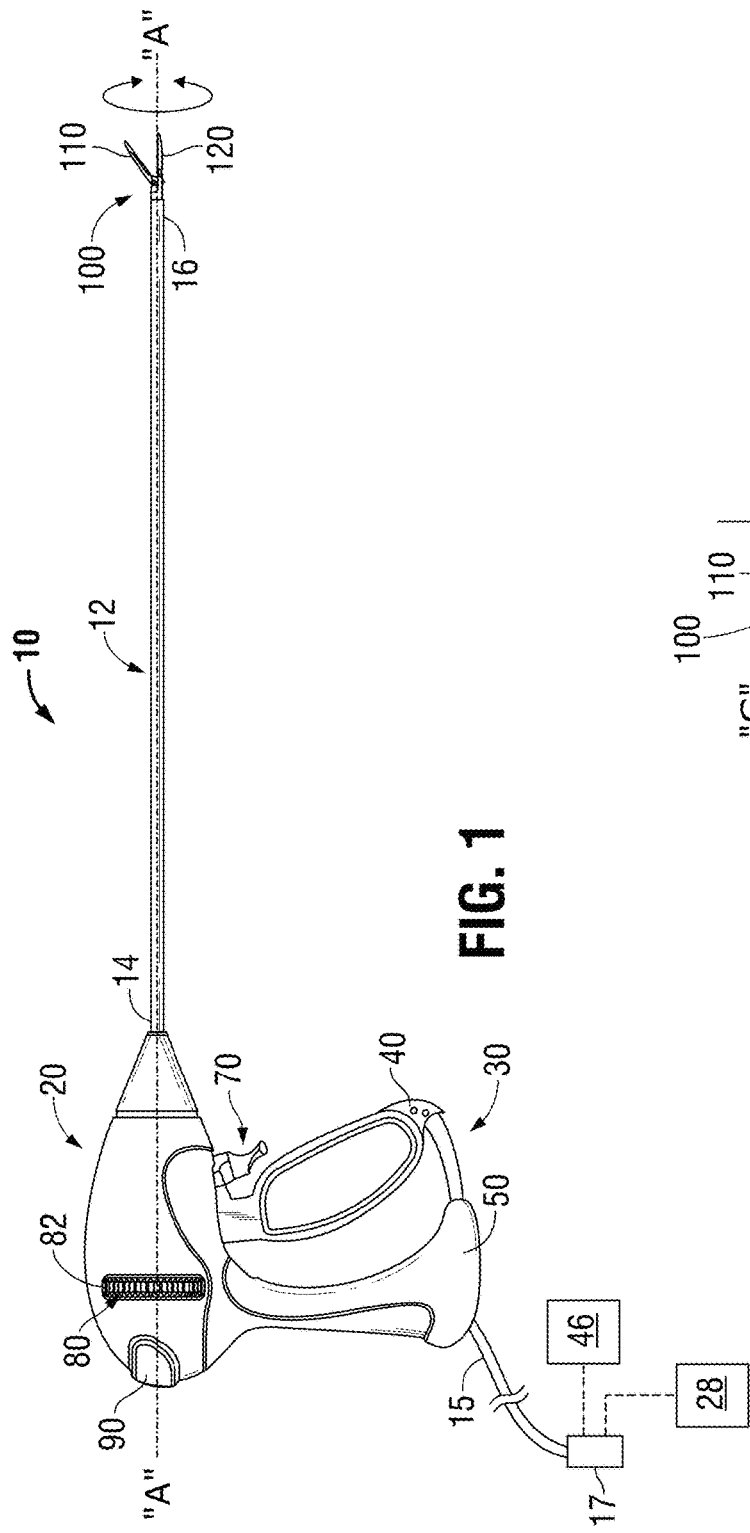
FIG. 1 is a left, perspective view of an endoscopic bipolar forceps showing a housing, a rotatable member, a shaft and an end-effector assembly having first and second jaw members including temperature-sensing electrically-conductive tissue-contacting plates in accordance with an embodiment of the present disclosure.

Hereinafter, embodiments of a temperature-sensing electrically-conductive tissue-contacting plate configured for use in an electrosurgical end-effector assembly, electrosurgical systems including the same, and methods of controlling vessel sealing using the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "electrically-conductive tissue-contacting plate" generally refers to an electrically-conductive member including one or more tissue engaging surfaces that can be used to transfer energy from an electrosurgical power generating source, such as RF electrosurgical generator, to tissue. As it is used in this description, "electrically conductive", or simply "conductive", generally refers to materials that are capable of electrical conductivity, including, without limitation, materials that are highly conductive, e.g., metals and alloys, or materials that are semi-conductive, e.g., semi-conducting materials and composites. As it is used in this description, "transmission line" generally refers to any transmission medium that can be used for the propagation of signals from one point to another.

Vessel sealing or tissue sealing utilizes a combination of radiofrequency energy, pressure and gap control to effectively seal or fuse tissue between two opposing jaw members or sealing plates thereof. Vessel or tissue sealing is more than "cauterization" which may be defined as the use of heat to destroy tissue (also called "diathermy" or "electrodiathermy"), and vessel sealing is more than "coagulation" which may be defined as a process of desiccating tissue wherein the tissue cells are ruptured and dried. As it is used in this description, "vessel sealing" generally refers to the process of liquefying the collagen, elastin and ground substances in the tissue so that it reforms into a fused mass with significantly-reduced demarcation between the opposing tissue structures.

Various embodiments of the present disclosure provide electrosurgical instruments suitable for sealing, cauterizing, coagulating, desiccating, and/or cutting tissue, e.g., vessels and vascular tissue, during a surgical procedure. Embodiments of the presently-disclosed electrosurgical instruments may be suitable for utilization in endoscopic surgical procedures and/or suitable for utilization in open surgical applications. Embodiments of the presently-disclosed electrosurgical instruments may be implemented using electrosurgical energy at radio frequencies (RF) and/or at other frequencies.

Various embodiments of the present disclosure provide electrosurgical instruments that include an end-effector assembly having jaw members including a temperature-sensing electrically-conductive tissue-contacting plate including one or more temperature sensors coupled to a bottom surface thereof. One or more operating parameters associated with an electrosurgical power generating source may be controlled based on one or more signals indicative of a temperature sensed by the one or more temperature sensors coupled to the bottom surface of each one of the temperature-sensing electrically-conductive tissue-contacting plates. The presently-disclosed tissue-contacting plate embodiments may include a plurality of zones, wherein each zone includes one or more temperature sensors (and/or pressure sensors), e.g., to provide feedback to an electrosurgical power generating source configured to turn on/off different zones to provide more uniform heating patterns across the jaw members and/or to help control thermal spread.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end-effectors, graspers, knifes, scissors, etc.) which may complement the use of one or more of the embodiments described herein. In various embodiments disclosed herein, an end-effector assembly may be coupled to a pair of master handles by a controller. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the jaw members onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although the following description describes the use of an endoscopic bipolar forceps, the teachings of the present disclosure may also apply to a variety of electrosurgical devices that include an end-effector assembly.

Figure 2:
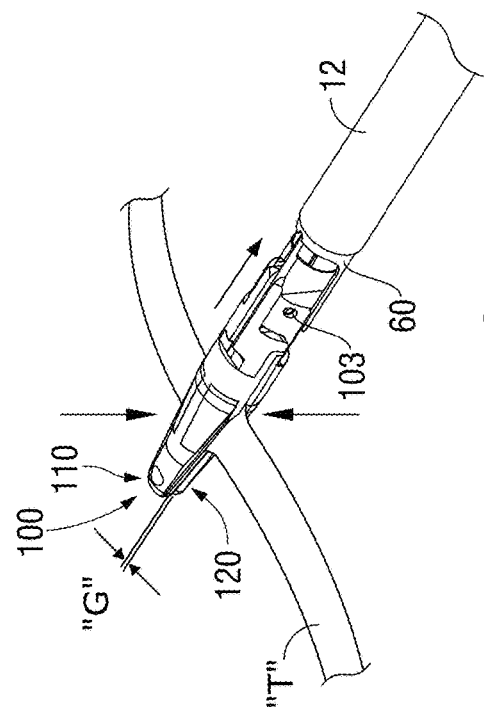
FIG. 2 is an enlarged, perspective view of the end-effector assembly of FIG. 1 shown grasping tissue.

In FIG. 1, an embodiment of an electrosurgical instrument 10, e.g., an endoscopic bipolar forceps, is shown for use with various surgical procedures and generally includes a housing 20, a handle assembly 30, a rotatable assembly 80, a trigger assembly 70 and an end-effector assembly 100 that mutually cooperate to grasp, seal and/or divide tubular vessels and vascular tissue (e.g., "T" shown in FIG. 2). Handle assembly 30 includes a fixed handle 50 and a movable handle 40. Although FIG. 1 depicts a bipolar forceps 10 for use in connection with endoscopic surgical procedures, the teachings of the present disclosure may also apply to more traditional open surgical procedures. For the purposes herein, the device 10 is described in terms of an endoscopic instrument; however, it is contemplated that an open version of a forceps (e.g., open bipolar forceps 300 shown in FIG. 3) may also include the same or similar operating components and features as described below.

As shown in FIG. 1, the shaft 12 includes a distal end 16 configured to mechanically engage the end-effector assembly 100. In some embodiments, the end-effector assembly 100 is selectively and releasably engageable with the distal end 16 of the shaft 12. The proximal end 14 of the shaft 12 is received within the housing 20, and connections relating thereto are shown and described in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS," and commonly assigned U.S. Pat. No. 7,771,425 entitled "VESSEL SEALER AND DIVIDER HAVING A VARIABLE JAW CLAMPING MECHANISM."

End-effector assembly 100 generally includes a pair of opposing jaw members 110 and 120 movably mounted with respect to one another. End-effector assembly 100 is configured as a unilateral assembly, i.e., the end-effector assembly 100 includes a stationary or fixed jaw member 120 mounted in fixed relation to the shaft 12 and a pivoting jaw member 110 mounted about a pivot pin 103 coupled to the stationary jaw member 120. Alternatively, the forceps 10 may include a bilateral jaw assembly, i.e., both jaw members move relative to one another.

Figure 5:
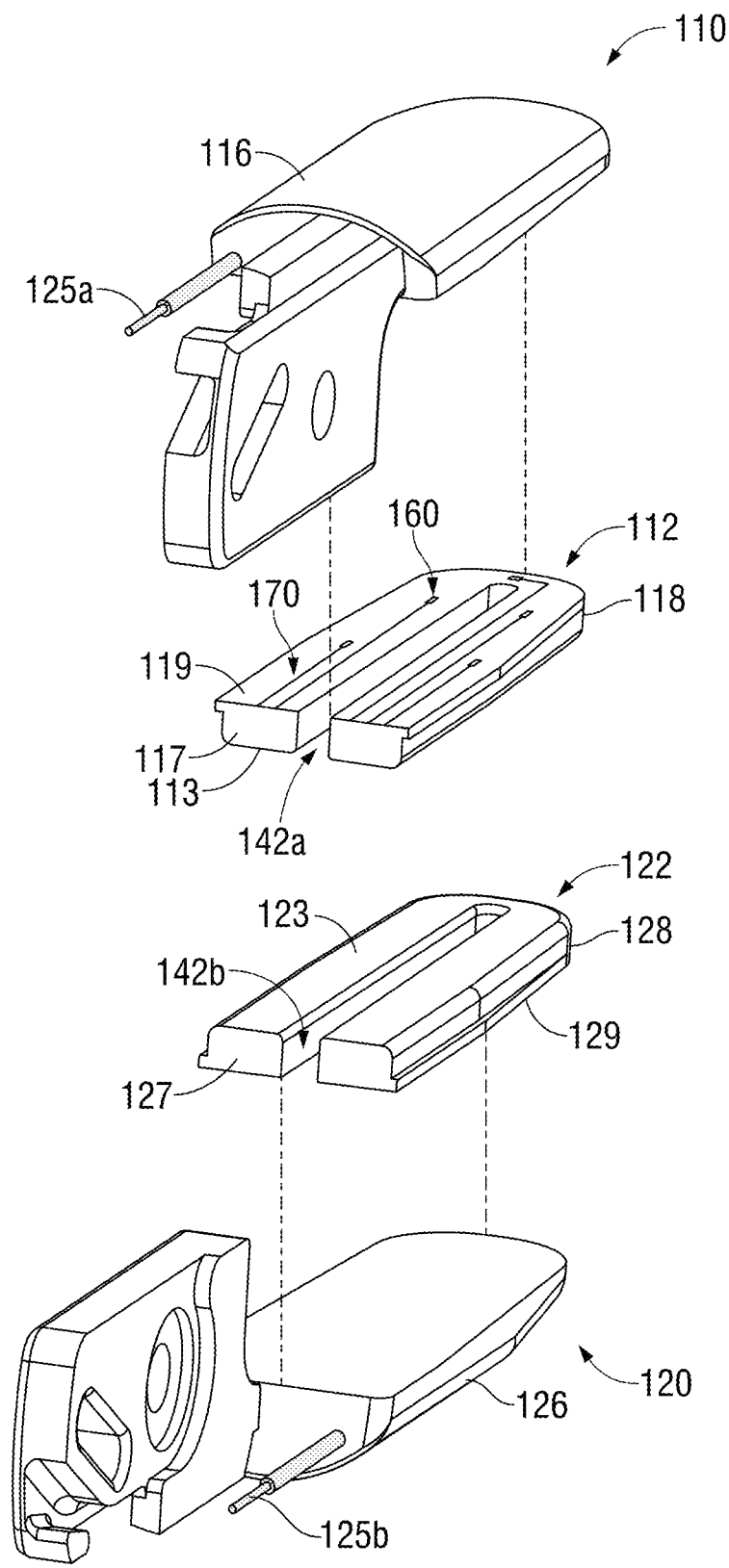
FIG. 5 is an enlarged, perspective view of first and second jaw members of the end-effector assembly of FIG. 1, shown with parts separated, illustrating a first configuration of a sensor arrangement associated with the temperature-sensing electrically-conductive tissue-contacting plate of the first jaw member in accordance with an embodiment of the present disclosure.

As shown in FIG. 5, the jaw members 110 and 120 include a structural support member 116 and 126, respectively, and a temperature-sensing electrically-conductive tissue-contacting plate 112 and 122, respectively. Temperature-sensing electrically-conductive tissue-contacting plate 112 includes a tissue-contacting surface 113, a bottom surface 119, and a slot 142a defined therethrough. Temperature-sensing electrically-conductive tissue-contacting plate 122 includes a tissue-contacting surface 123, a bottom surface 129, and a slot 142b defined therethrough.

The structural support members 116 and 126 are configured to mechanically engage the bottom surfaces 119 and 129, respectively. Structural support members 116 and 126 may be manufactured from any suitable materials, e.g., metal, plastic and the like.

Slots 142a and 142b extend distally from a proximal end 117 and 127, respectively, of the temperature-sensing electrically-conductive tissue-contacting plates 112 and 122 and provide a path for longitudinal translation of a knife blade (not shown) therein. In some embodiments, the temperature-sensing electrically-conductive tissue-contacting plates 112 and 122 are configured in such a manner that when the jaw members 110 and 120 are in a closed configuration, a knife blade (not shown), or portion thereof, is translatable within a knife channel formed by the slot 142a of temperature-sensing electrically-conductive tissue-contacting plate 112 and the slot 142b of temperature-sensing electrically-conductive tissue-contacting plate 122.

In some embodiments, as shown in FIG. 2, slots 142a and 142b are open at the bottom surface 119 and 129 of their respective temperature-sensing electrically-conductive tissue-contacting plates 112 and 122. In other embodiments, slots 142a and 142b may be closed at the bottom surface of their respective temperature-sensing electrically-conductive tissue-contacting plates 112 and 122.

In some embodiments, the temperature-sensing electrically-conductive tissue-contacting plates 112 and 122 may have a thickness that varies (i.e., non-uniform) from a proximal end 117 and 127 to a distal end 118 and 128, respectively. For example, temperature-sensing electrically-conductive tissue-contacting plates 112 and 122 each may have a proximal end 117 and 127, respectively, having a thickness that is slightly larger than a thickness at the distal end 118 and 128 thereof, e.g., depending on a particular purpose.

Jaw members 110 and 120 are electrically isolated from one another. End-effector assembly 100 (FIG. 1) may additionally, or alternatively, include electrically-insulative members and/or electrically-insulative, thermally non-degrading coatings configured to electrically isolate, at least in part, the temperature-sensing electrically-conductive tissue-contacting plates 112 and 122 from the jaw members 110 and 120, respectively.

As shown in FIG. 1, the end-effector assembly 100 is rotatable about a longitudinal axis "A-A" defined through shaft 12, either manually or otherwise, by the rotatable assembly 80. Rotatable assembly 80 generally includes two halves (not shown), which, when assembled, form a generally circular rotatable member 82. Rotatable assembly 80, or portions thereof, may be configured to house a drive assembly (not shown) and/or a knife assembly (not shown), or components thereof. Examples of rotatable assembly embodiments, drive assembly embodiments, knife assembly embodiments, and handle assembly embodiments of the electrosurgical instrument 10 are shown and described in the above-mentioned, commonly-assigned U.S. Pat. Nos. 7,150,097, 7,156,846, 7,597,693 and 7,771,425.

Electrosurgical instrument 10 includes a switch 90 configured to permit the user to selectively activate the instrument 10 in a variety of different orientations, i.e., multi-oriented activation. When the switch 90 is depressed, electrosurgical energy is transferred through one or more electrical leads (e.g., leads 125a and 125b shown in FIG. 5) to the jaw members 110 and 120.

Forceps 10 includes an electrosurgical cable 15 formed from a suitable flexible, semi-rigid or rigid cable, and may connect directly to an electrosurgical power generating source 28, e.g., a microwave or RF electrosurgical generator. In some embodiments, the electrosurgical cable 15 connects the forceps 10 to a connector 17, which further operably connects the instrument 10 to the electrosurgical power generating source 28.

Electrosurgical power generating source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, SURGISTAT™ II, and FORCE TRIAD™ offered by Covidien. Forceps 10 may alternatively be configured as a wireless device or battery-powered.

FIG. 2 shows the end-effector assembly 100 of FIG. 1 shown grasping tissue T. In some embodiments, the end-effector assembly 100 may include a gap distance "G" between opposing sealing surfaces 112 during sealing, e.g., in the range from about 0.001 inches to about 0.006 inches. In some embodiments, the end-effector assembly 100 includes a gap distance "G" between opposing tissue-contacting surfaces during sealing that ranges from about 0.002 to about 0.003 inches.

As energy is being selectively transferred to the end-effector assembly 100, across the jaw members 110 and 120 and through the tissue "T", a tissue seal forms isolating two tissue halves (not shown). A knife assembly (not shown) which, when activated via the trigger assembly 70, progressively and selectively divides the tissue "T" along a tissue plane in a precise manner to divide the tissue "T" into two sealed halves (not shown). Once the tissue "T" is divided into tissue halves (not shown), the jaw members 110 and 120 may be opened by re-initiation or re-grasping of the handle 40.

Figure 3:
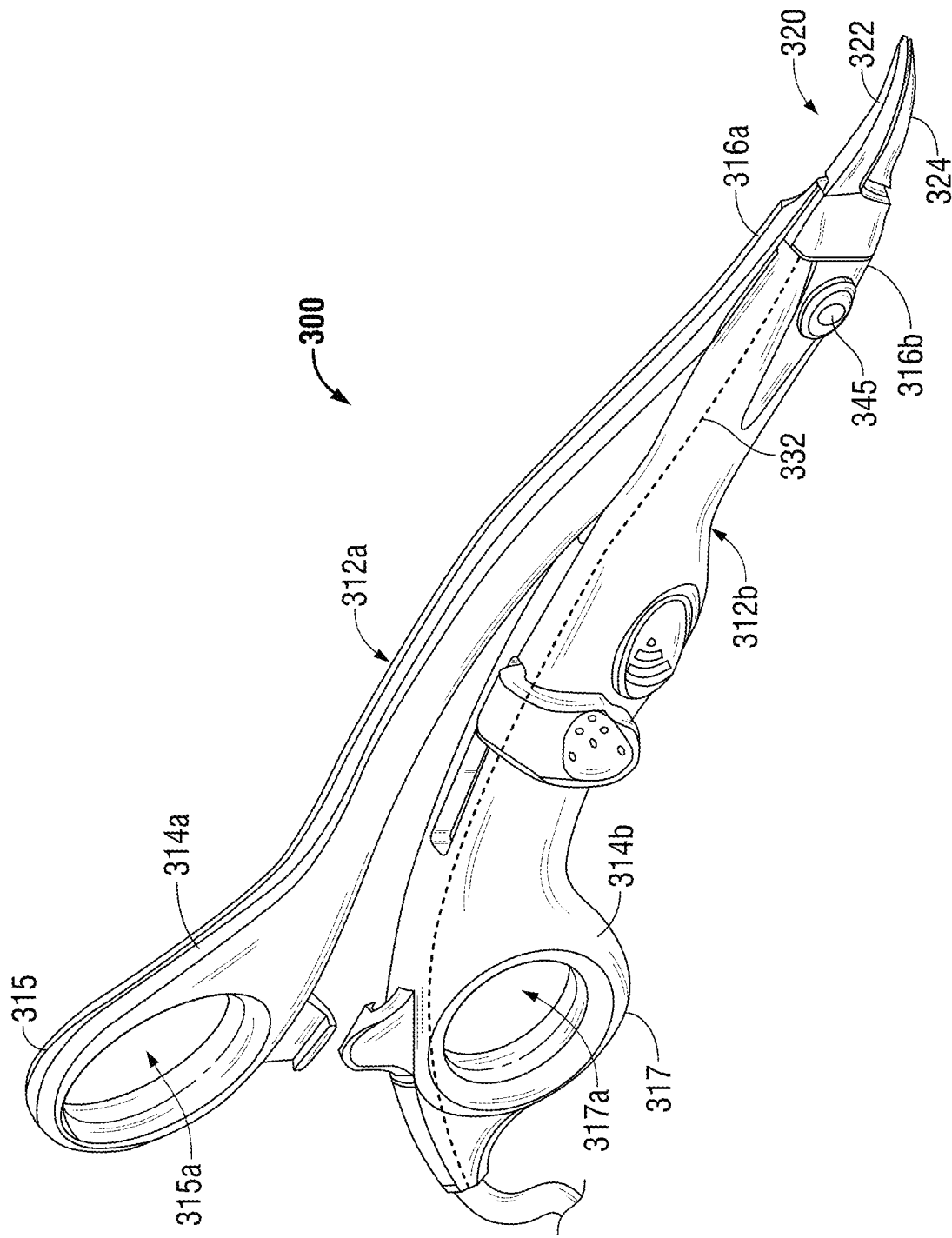
FIG. 3 is a perspective view of an open bipolar forceps in accordance with an embodiment of the present disclosure.

In FIG. 3, an open forceps 300 is shown for use with various surgical procedures and generally includes a pair of opposing shafts 312a and 312b having an end-effector assembly 320 attached to the distal ends 316a and 316b thereof, respectively. End-effector assembly 320 is similar in design to the end-effector assembly 100 and includes a pair of opposing jaw members 322 and 324 that are pivotably connected about a pivot pin 365 and movable relative to one another to grasp tissue. Each shaft 312a and 312b includes a handle 315 and 317, respectively, disposed at the proximal end 314a and 314b thereof which each define a finger and/or thumb hole 315a and 317a, respectively, therethrough for receiving the user's finger or thumb. Finger and/or thumb holes 315a and 317a facilitate movement of the shafts 312a and 312b relative to one another pivot the jaw members 322 and 324 from an open position, wherein the jaw members 322 and 324 are disposed in spaced relation relative to one another, to a clamping or closed position, wherein the jaw members 322 and 324 cooperate to grasp tissue therebetween. End-effector assembly 320 may include any feature or combination of features of the temperature-sensing seal plate embodiments disclosed herein.

Figure 4:
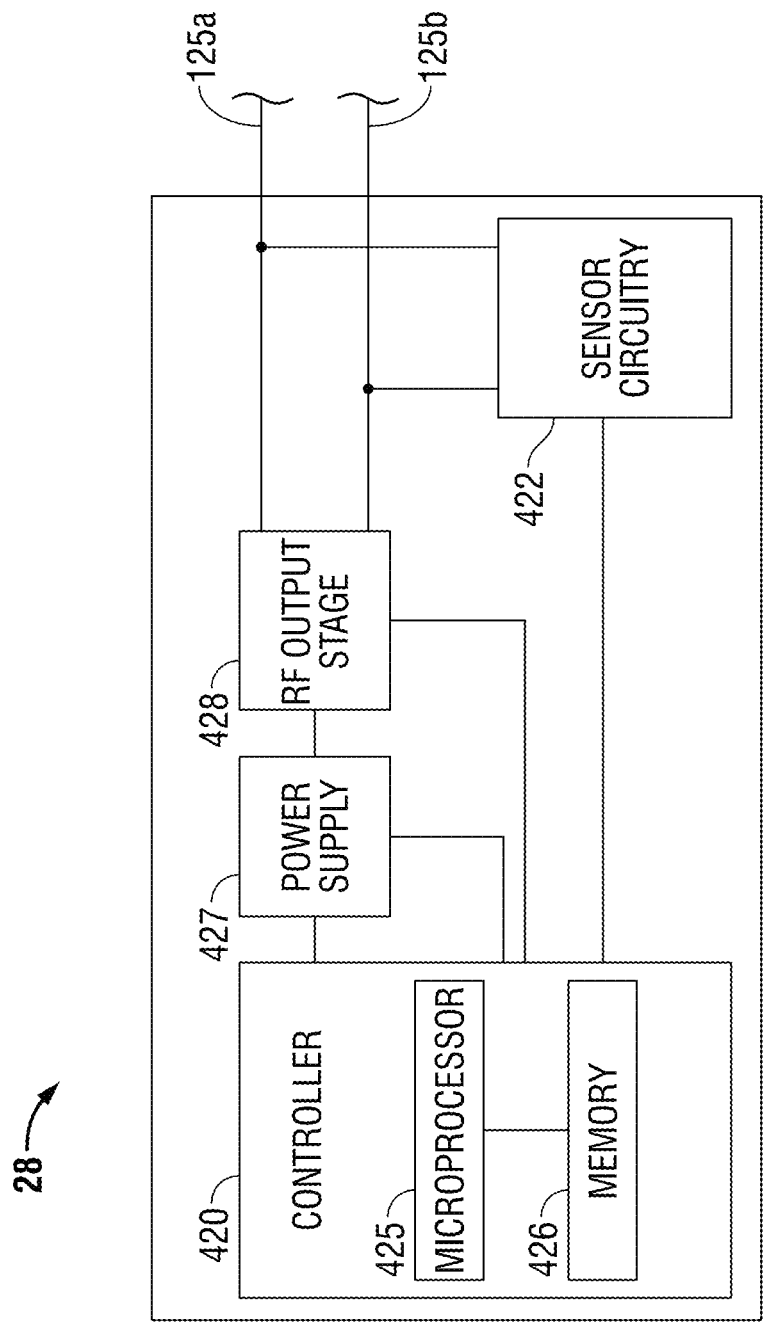
FIG. 4 is a schematic block diagram of an electrosurgical system in accordance with an embodiment of the present disclosure.

FIG. 4 shows a schematic block diagram of the electrosurgical power generating source 28 of FIG. 1 including a controller 420, a power supply 427, an RF output stage 428, and a sensor module 422. In some embodiments, as shown in FIG. 4, the sensor module 422 is formed integrally with the electrosurgical power generating source 28. In other embodiments, the sensor module 422 may be provided as a separate circuitry coupled to the electrosurgical power generating source 28. The power supply 427 provides DC power to the RF output stage 428 which then converts the DC power into RF energy and delivers the RF energy to the instrument 10 (FIG. 1). The controller 420 includes a microprocessor 425 having a memory 426 which may be volatile type memory (e.g., RAM) and/or non-volatile type memory (e.g., flash media, disk media, etc.). The microprocessor 425 includes an output port connected to the power supply 427 and/or RF output stage 428 that allows the microprocessor 425 to control the output of the generator 400 according to either open and/or closed control loop schemes.

A closed loop control scheme generally includes a feedback control loop wherein the sensor module 422 provides feedback to the controller 420 (e.g., information obtained from one or more sensing mechanisms for sensing various tissue parameters such as tissue impedance, tissue temperature, output current and/or voltage, etc.). The controller 420 then signals the power supply 427 and/or RF output stage 428 which then adjusts the DC and/or RF power supply, respectively. The controller 420 also receives input signals from the input controls of the electrosurgical power generating source 28 and/or instrument 10 (FIG. 1). The controller 420 utilizes the input signals to adjust one or more operating parameters associated with the electrosurgical power generating source 28 and/or instructs the electrosurgical power generating source 28 to perform other control functions.

The microprocessor 425 is capable of executing software instructions for processing data received by the sensor module 422, and for outputting control signals to the electrosurgical power generating source 28, accordingly. The software instructions, which are executable by the controller 420, are stored in the memory 426 of the controller 420.

The controller 420 may include analog and/or logic circuitry for processing the sensed values and determining the control signals that are sent to the electrosurgical power generating source 28, rather than, or in combination with, the microprocessor 425. The sensor module 422 may include a plurality of sensors (not shown) strategically located for sensing various properties or conditions, e.g., tissue impedance, voltage at the tissue site, current at the tissue site, etc. The sensors are provided with leads (or wireless) for transmitting information to the controller 420. The sensor module 422 may include control circuitry that receives information from multiple sensors, and provides the information and the source of the information (e.g., the particular sensor providing the information) to the controller 420.

In some embodiments, the controller 420 is configured to control one or more operating parameters associated with the electrosurgical power generating source 28 based on one or more signals indicative of a sensed temperature in one or more zones of the presently-disclosed temperature-sensing electrically-conductive tissue-contacting plate, e.g., the outer zone "$Z_{OUT}$" (FIG. 11) to regulate thermal spread. In some embodiments, as shown in FIG. 4, the controller 420 is formed integrally with the electrosurgical power generating source 28. In other embodiments, the controller 420 may be provided as a separate component coupled to the electrosurgical power generating source 28.

Figure 6:
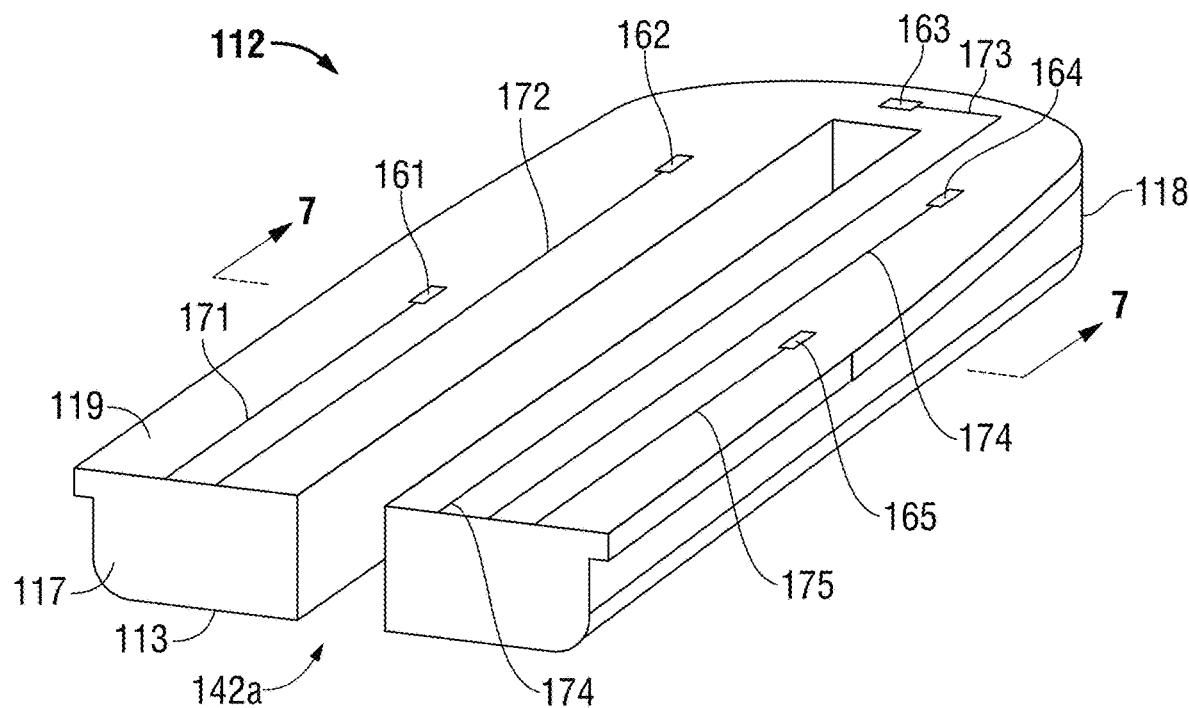
FIG. 6 is an enlarged, perspective view of the temperature-sensing electrically-conductive tissue-contacting plate of the first jaw member shown in FIG. 5.

As shown in FIGS. 5 and 6, the temperature-sensing electrically-conductive tissue-contacting plate 112 of the first jaw member 110 includes a configuration of a plurality of sensors located on the bottom surface 119 thereof. As seen in FIG. 6, the temperature-sensing electrically-conductive tissue-contacting plate 112 includes a first sensor 161, a second sensor 162, a third sensor 163, a fourth sensor 164, and a fifth sensor 165 disposed on the bottom surface 119. The first and second sensors 161 and 162 are disposed in spaced relation relative to one another on the bottom surface 119 along one side of the slot 142a, and the fourth and fifth sensors 164 and 165 are disposed in spaced relation relative to one another on the bottom surface 119 along the opposite side of the slot 142a. The third sensor 163 is disposed on the bottom surface 119 proximate the distal end 118 of the temperature-sensing electrically-conductive tissue-contacting plate 112.

In some embodiments, the first, second, third, fourth and fifth sensors 161, 162, 163, 164 and 165, respectively, are temperature sensors, e.g., thermocouples and/or thermistors. One or more of the sensors 161-165 may be a thermocouple that includes one or more deposited layers formed utilizing vapor deposition. Additionally, or alternatively, one or more of the first, second, third, fourth and fifth sensors 161, 162, 163, 164 and 165, respectively, may be J-type thermocouples; however, it is to be understood that any suitable type of thermocouple may be utilized.

In some embodiments, the first, second, third, fourth and fifth sensors 161, 162, 163, 164 and 165, respectively, are electrically coupled to first, second, third, fourth and fifth electrically-conductive traces 171, 172, 173, 174 and 175, respectively. A variety of trace geometries may be used, e.g., planar conductor lines.

Figure 8:
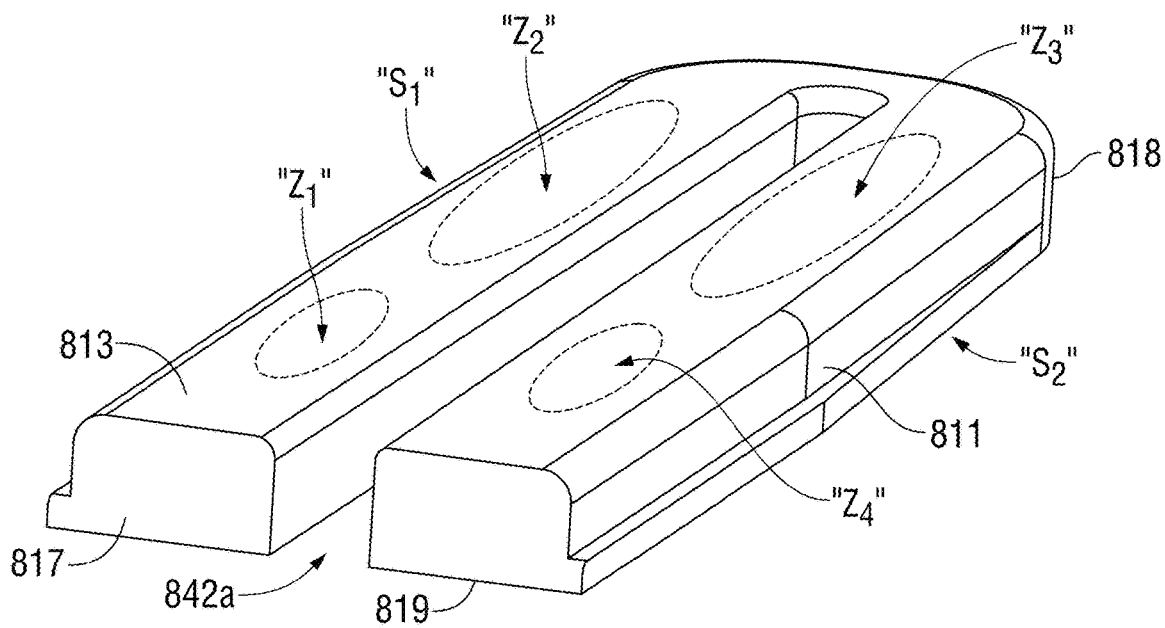
FIG. 8 is an enlarged, perspective view of a temperature-sensing electrically-conductive tissue-contacting plate illustrating a first configuration of zones, e.g., heating zones, as indicated by dashed lines, on the tissue-contacting surface thereof in accordance with an embodiment of the present disclosure.
Figure 9:
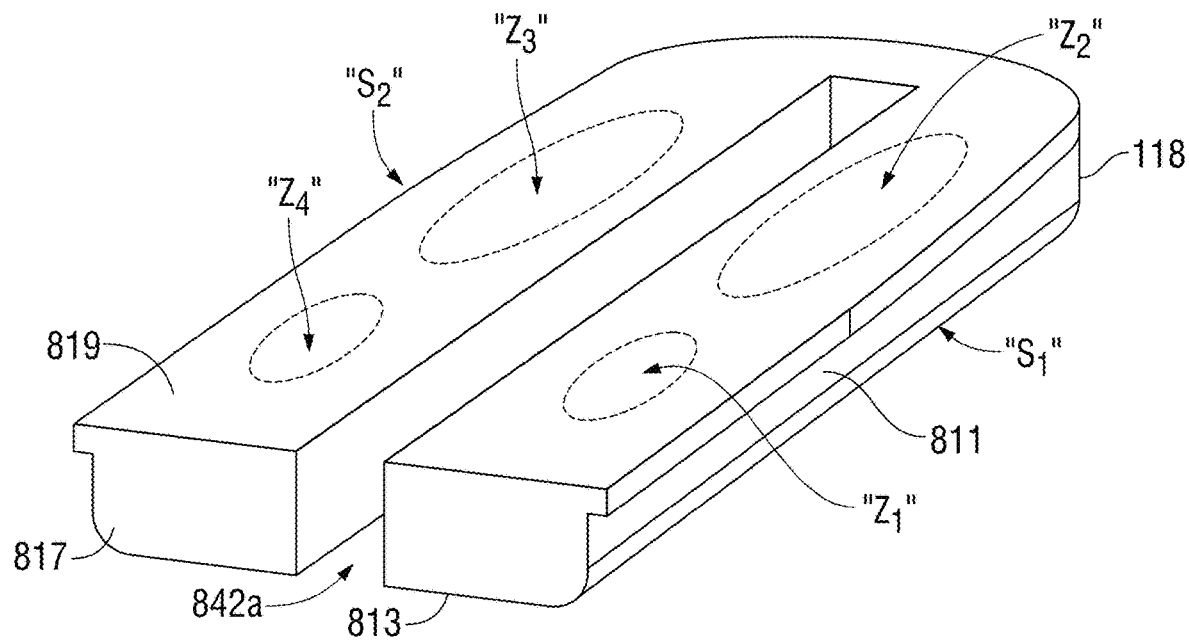
FIG. 9 is an enlarged, perspective view of the temperature-sensing electrically-conductive tissue-contacting plate shown in FIG. 8, illustrating a first configuration of zones, as indicated by dashed lines, on the bottom surface thereof in accordance with an embodiment of the present disclosure.

FIGS. 8 and 9 show a temperature-sensing electrically-conductive tissue-contacting plate 811 having a proximal end 817, a distal end 818, a tissue-contacting surface 813, a bottom surface 819, and a slot 842a defined therethrough. FIG. 8 shows a first configuration of zones, e.g., heating zones, as indicated by dashed lines, on the tissue-contacting surface 813 thereof. FIG. 9 shows a first configuration of zones, as indicated by dashed lines, on the bottom surface 819 of the temperature-sensing electrically-conductive tissue-contacting plate 811.

Figure 10:
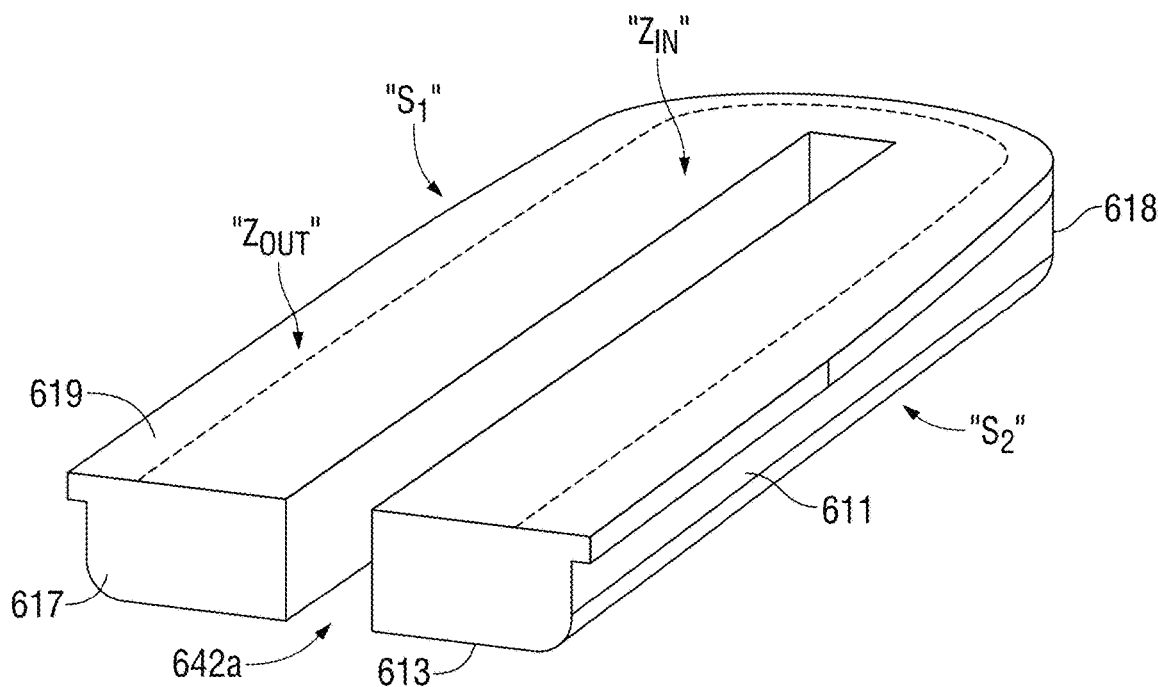
FIG. 10 is an enlarged, perspective view a temperature-sensing electrically-conductive tissue-contacting plate, illustrating a second configuration of zones, as indicated by the generally U-shaped dashed line, in accordance with an embodiment of the present disclosure.

FIG. 10 shows a partial, temperature-sensing electrically-conductive tissue-contacting plate including a second configuration of zones. As seen in FIG. 10, a bottom surface 619 of an electrically-conductive substrate 611 is arranged into two different regions or zones, as indicated by the generally U-shaped dashed line in FIG. 10. For ease of understanding, the region around the periphery of the bottom surface 619 disposed outwardly of the dashed line in FIGS. 10 and 11 is referred to herein as the outer zone "$Z_{OUT}$", and the region disposed inwardly of the dashed line in FIGS. 10 and 11 is referred to herein as the inner zone "$Z_{IN}$".

Figure 11:
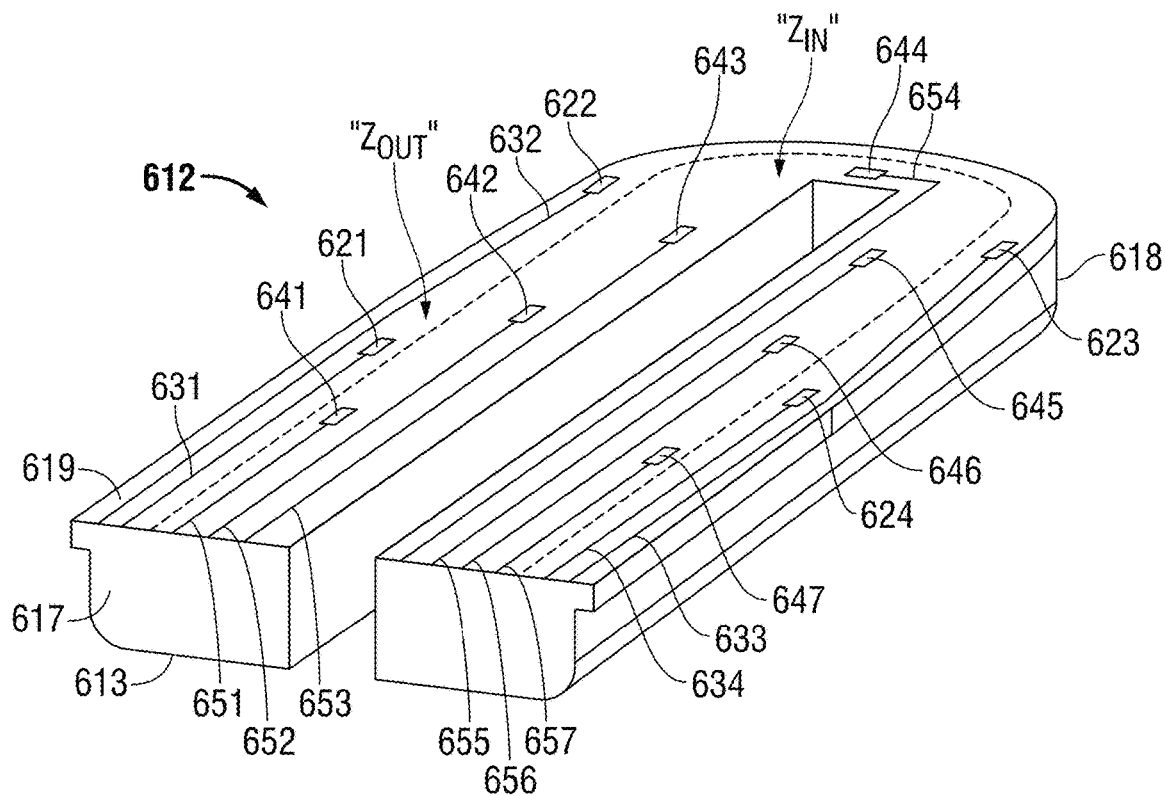
FIG. 11 is an enlarged, perspective view of the temperature-sensing electrically-conductive tissue-contacting plate of FIG. 10 illustrating a dual zone sensor arrangement on the bottom surface thereof in accordance with an embodiment of the present disclosure.

FIG. 11 shows a temperature-sensing electrically-conductive tissue-contacting plate 612 that includes a tissue-contacting surface 613 and a bottom surface 619. The tissue-contacting surface 613 may be curved or straight depending upon a particular surgical purpose. For example, the tissue-contacting surface 613 may be curved at various angles to facilitate manipulation of tissue and/or to provide enhanced line-of-sight for accessing targeted tissues. In some embodiments, the temperature-sensing electrically-conductive tissue-contacting plate 612 may have a thickness that varies (i.e., non-uniform) from a proximal end 617 to a distal end 618 thereof.

Temperature-sensing electrically-conductive tissue-contacting plate 612 includes a plurality of sensors associated with the bottom surface 619 thereof. One or more sensors, e.g., temperature sensors, may be disposed within the outer zone "$Z_{OUT}$" and/or one or more sensors, e.g., temperature sensors, may be disposed within the inner zone "$Z_{IN}$". In some embodiments, as shown in FIG. 6, a first sensor 621, a second sensor 622, a third sensor 623 and a fourth sensor 624 are disposed within the outer zone "$Z_{OUT}$", and a first sensor 641, a second sensor 642, a third sensor 643, a fourth sensor 644, a fifth sensor 645, a sixth sensor 646 and a seventh sensor 647 are disposed within the inner zone "$Z_{IN}$". The first, second, third and fourth sensors 621, 622, 623 and 624, respectively, are electrically coupled to first, second, third and fourth electrically-conductive traces 631, 632, 633 and 634, respectively. The first, second, third, fourth, fifth, sixth and seventh sensors 641, 642, 643, 644, 645, 646 and 647, respectively, are electrically coupled to first, second, third, fourth, fifth, sixth and seventh electrically-conductive traces 651, 652, 653, 654, 655, 656 and 657, respectively.

In some embodiments, the sensors 621-624 and/or the sensors 641-647 include thermocouples and/or thermistors. In some embodiments, the sensors 621-624 and/or the sensors 641-647 may include J-type thermocouples, but it is to be understood that any suitable type of thermocouple may be utilized. In alternative embodiments, one or more of the sensors 621-624 and/or one or more of the sensors 641-647 may include pressure sensors (e.g., piezo sensors, multilayer bending sensors, etc.).

Figure 12:
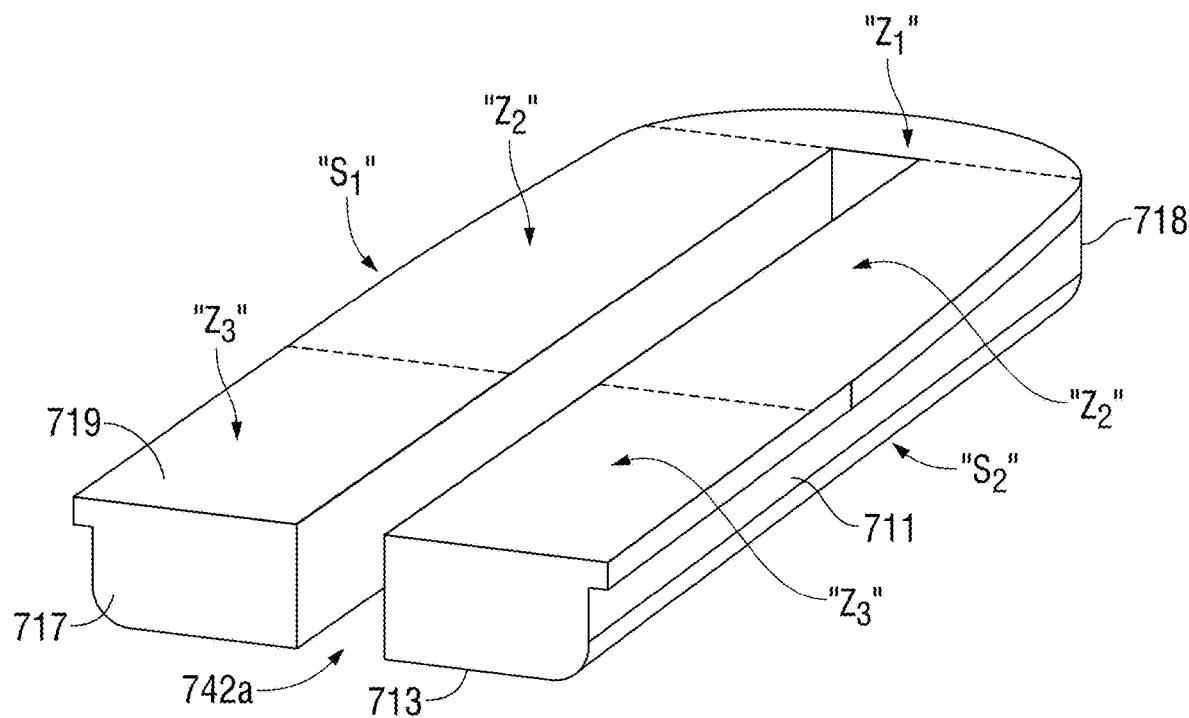
FIG. 12 is an enlarged, perspective view of a temperature-sensing electrically-conductive tissue-contacting plate illustrating a third configuration of zones in accordance with an embodiment of the present disclosure.

FIG. 12 shows a partial, temperature-sensing electrically-conductive tissue-contacting plate including a third configuration of zones, as indicated by the dashed lines. In FIG. 12, three heating zones, "$Z_1$", "$Z_2$", and "$Z_3$", are shown on an electrically-conductive substrate 711.

Figure 13:
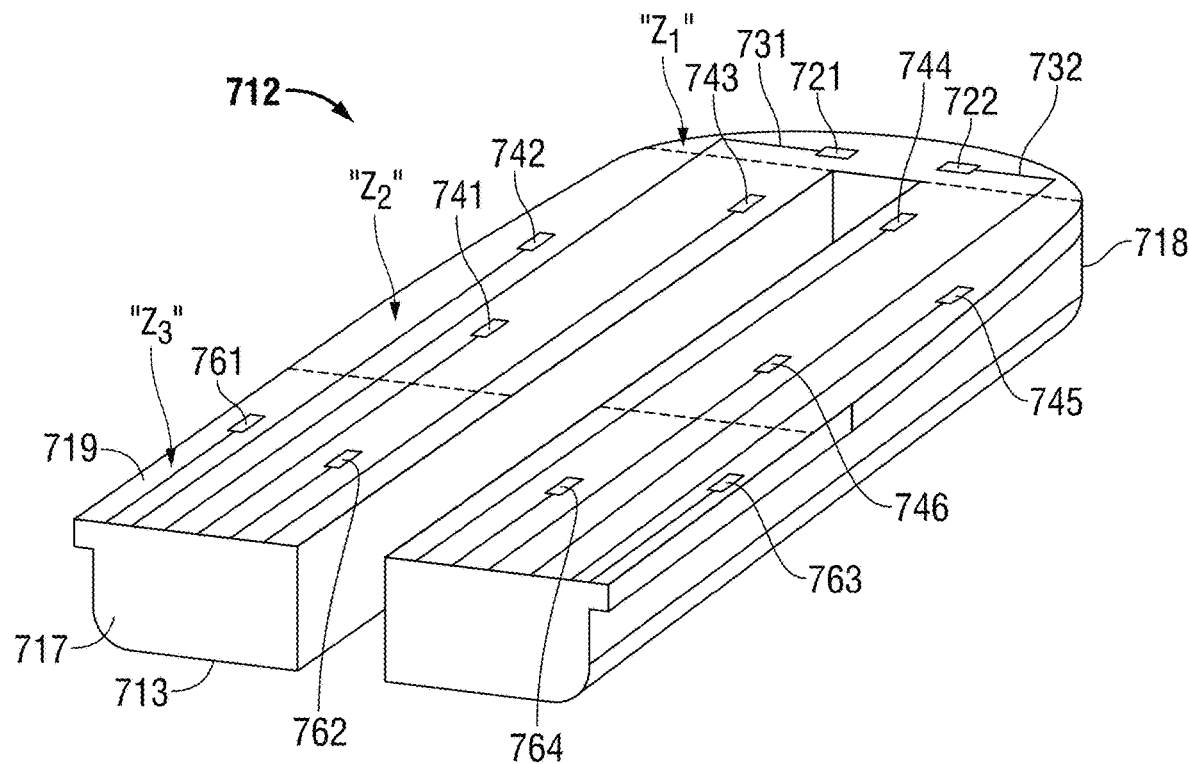
FIG. 13 is an enlarged, perspective view of the temperature-sensing electrically-conductive tissue-contacting plate of FIG. 12 illustrating a multi-zone configuration of a sensor arrangement on the bottom surface thereof in accordance with an embodiment of the present disclosure.

FIG. 13 shows a temperature-sensing electrically-conductive tissue-contacting plate 712 having a proximal end 717, a distal end 718, a tissue-contacting surface 713, and a bottom surface 719. Temperature-sensing electrically-conductive tissue-contacting plate 712 includes a plurality of sensors associated with the bottom surface 719 thereof. As seen FIG. 13, bottom surface 719 includes three different regions or zones, as indicated by the dashed lines in FIG. 7. The region at a distal end portion of the bottom surface 719 is referred to herein as the first zone "$Z_1$", the middle region is referred to herein as the second zone "$Z_2$", and the region at a proximal end portion or "heel" of the temperature-sensing electrically-conductive tissue-contacting plate 712 is referred to herein as the third zone "$Z_3$".

Figure 7:
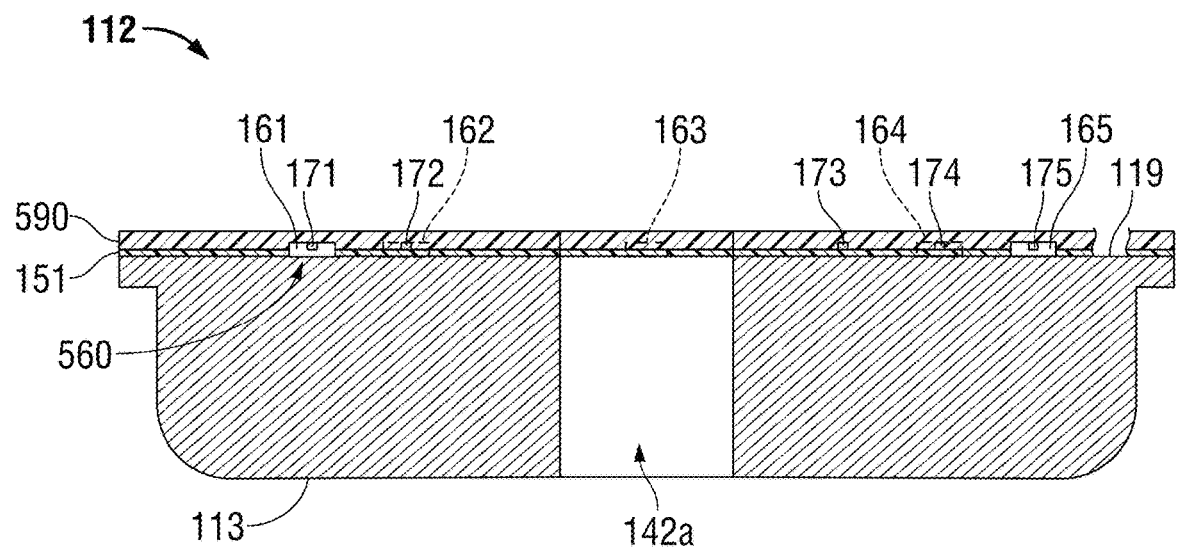
FIG. 7 is a cross-sectional view taken along the lines "7-7" of FIG. 6 illustrating a first configuration of a sensor arrangement associated with the temperature-sensing electrically-conductive tissue-contacting plate of the first jaw member in accordance with an embodiment of the present disclosure.

In some embodiments, as shown in FIG. 7, two sensors (e.g., a first sensor 721 and a second sensor 722) are disposed within the first zone "$Z_1$", six sensors (e.g., a first sensor 741, a second sensor 742, a third sensor 743, a fourth sensor 744, a fifth sensor 745 and a sixth sensor 746) are disposed within the second zone "$Z_2$", and four sensors (e.g., a first sensor 761, a second sensor 762, a third sensor 763 and a fourth sensor 764) are disposed within the third zone "$Z_3$". As seen in FIG. 7, a plurality of electrically-conductive traces is provided. For example, the first and second sensors 721 and 722, respectively, are electrically coupled to first and second electrically-conductive traces 731 and 732, respectively.

In some embodiments, the sensors 721-722, the sensors 741-746, and/or the sensors 761-764 may include temperature sensors (e.g., thermocouples, thermistors, etc.) and/or pressure sensors (e.g., piezo sensors, multilayer bending sensors, etc.).

Hereinafter, methods of controlling vessel sealing are described with reference to FIGS. 14 and 15. It is to be understood that the steps of the methods provided herein may be performed in combination and in a different order than presented herein without departing from the scope of the disclosure.

Figure 14:
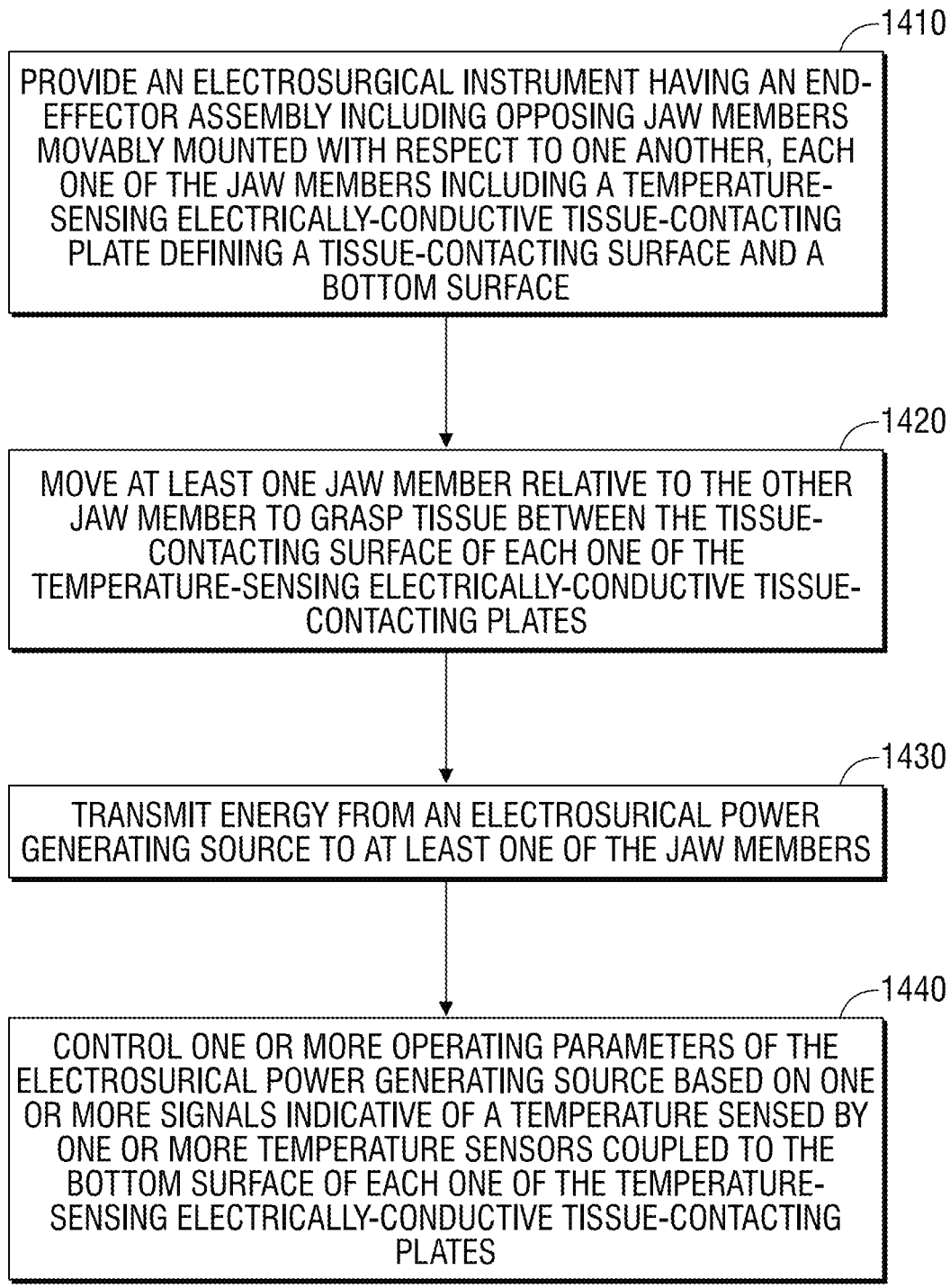
FIG. 14 is a flowchart illustrating a method of controlling vessel sealing in accordance with an embodiment of the present disclosure.

FIG. 14 is a flowchart illustrating a method of controlling vessel sealing according to an embodiment of the present disclosure. In step 1410, an electrosurgical instrument 10 is provided. The electrosurgical instrument 10 has an end-effector assembly 100 including opposing jaw members 110 and 120 movably mounted with respect to one another. The jaw members 110 and 120 each include a temperature-sensing electrically-conductive tissue-contacting plate 111 and 112, respectively. The temperature-sensing electrically-conductive tissue-contacting plates 111 and 112 each define a tissue-contacting surface 113 and 123 and a bottom surface 119 and 129, respectively.

In step 1420, at least one jaw member is moved relative to the other jaw member to grasp tissue "T" between the tissue-contacting surface 113 and 123 of each of the temperature-sensing electrically-conductive tissue-contacting plates 111 and 112, respectively.

In step 1430, energy from an electrosurgical power generating source 28 is transmitted to at least one of the jaw members 110, 120.

In step 1440, one or more operating parameters associated with the electrosurgical power generating source 28 are controlled based on one or more signals indicative of a temperature sensed by one or more temperature sensors 160 coupled to the bottom surface of each one of the temperature-sensing electrically-conductive tissue-contacting plates. Some examples of operating parameters associated with the electrosurgical power generating source 28 that may be adjusted include temperature, impedance, power, current, voltage, mode of operation, and duration of application of electrosurgical energy. In some embodiments, one or more operating parameters associated with the electrosurgical power generating source 28 are controlled based on one or more signals indicative of a sensed temperature in a plurality of zones (e.g., two zones "$Z_{OUT}$" and "$Z_{IN}$" shown in FIGS. 10 and 11, or three zones "$Z_1$", "$Z_2$", and "$Z_3$" shown in FIGS. 12 and 13) of the temperature-sensing electrically-conductive tissue-contacting plate.

Figure 15:
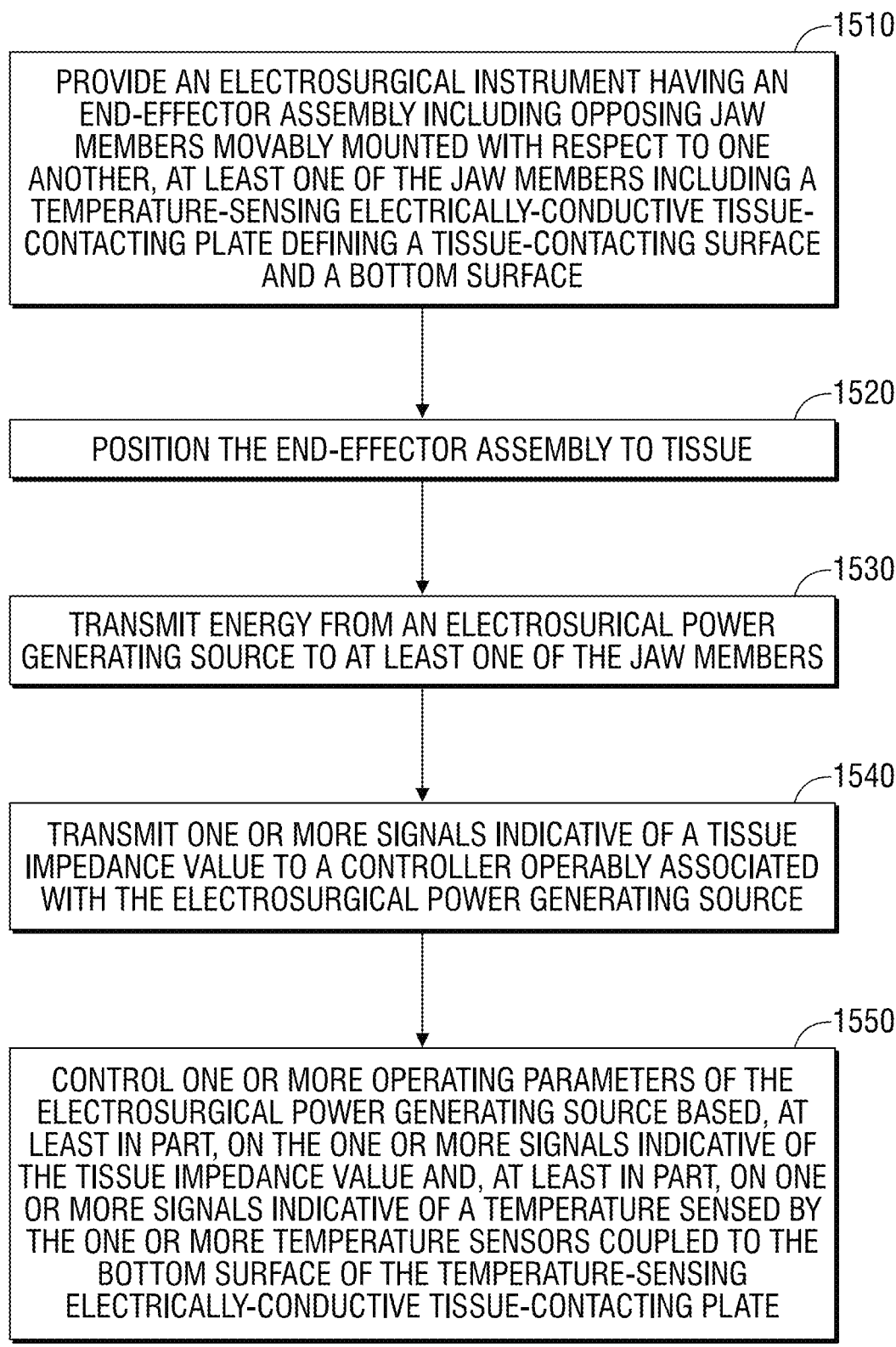
FIG. 15 is a flowchart illustrating a method of controlling vessel sealing in accordance with another embodiment of the present disclosure.

FIG. 15 is a flowchart illustrating a method of controlling vessel sealing according to an embodiment of the present disclosure. In step 1510, an electrosurgical instrument 10 is provided. The electrosurgical instrument 10 has an end-effector assembly 100 including opposing jaw members 110 and 120 movably mounted with respect to one another. At least one of the jaw members (e.g., jaw member 110) includes a temperature-sensing electrically-conductive tissue-contacting plate 111 defining a tissue-contacting surface 113 and a bottom surface 119.

In step 1520, the end-effector assembly 100 is positioned to tissue T. For example, the jaw members 110 and 120 are positioned to energize tissue T.

In step 1530, energy from an electrosurgical power generating source 28 is transmitted to at least one of the jaw members 110, 120.

In step 1540, one or more signals indicative of a tissue impedance value are transmitted to a controller 420 operably associated with the electrosurgical power generating source 28. Transmitting one or more signals indicative of a tissue impedance value may include measuring an impedance of tissue using a sensor module 422 coupled to the controller 420.

In step 1550, one or more operating parameters associated with the electrosurgical power generating source 28 are controlled based, at least in part, on the one or more signals indicative of the tissue impedance value and, at least in part, on one or more signals indicative of a temperature sensed by the one or more temperature sensors 160 coupled to the bottom surface 119 of the temperature-sensing electrically-conductive tissue-contacting plate 111. In some embodiments, one or more operating parameters associated with the electrosurgical power generating source 28 are controlled based on one or more signals indicative of a sensed temperature in a plurality of zones (e.g., two zones "$Z_{OUT}$" and "$Z_{IN}$" shown in FIGS. 10 and 11, or three zones "$Z_1$", "$Z_2$", and "$Z_3$" shown in FIGS. 12 and 13) of the temperature-sensing electrically-conductive tissue-contacting plate.

The presently-disclosed jaw members including a temperature-sensing electrically-conductive tissue-contacting plate are capable of directing energy into tissue, and may be suitable for use in a variety of procedures and operations. The above-described bipolar forceps embodiments may utilize both mechanical clamping action and electrical energy to effect hemostasis by heating tissue and blood vessels to coagulate, cauterize, cut and/or seal tissue. The jaw assemblies may be either unilateral or bilateral. The above-described bipolar forceps embodiments may be suitable for utilization with endoscopic surgical procedures and/or open surgical applications.

In the above-described bipolar forceps embodiments, the temperature-sensing electrically-conductive tissue-contacting plates may be used to ensure that tissue has been properly sealed, e.g., by providing a temperature measurement to a controller for use in determining that the tissue has met a minimum threshold temperature for tissue sealing.

The above-described temperature-sensing electrically-conductive tissue-contacting plates may be curved at various angles to facilitate manipulation of tissue and/or to provide enhanced line-of-sight for accessing targeted tissues. In some embodiments, the temperature-sensing electrically-conductive tissue-contacting plate may have a thickness that varies (i.e., non-uniform) from a proximal end to a distal end thereof.

The above-described tissue-contacting plate embodiments may include a plurality of zones, wherein each zone includes one or more sensors, including temperature sensors and/or pressure sensors, e.g., to provide feedback to an electrosurgical power generating source and/or a controller configured to turn on/off different zones to provide more uniform heating patterns across the jaw members and/or to help control thermal spread.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical system, comprising:
   an electrosurgical instrument, including:
      a housing; and
      a shaft extending from the housing and including a distal end configured to support an end-effector assembly, the end-effector assembly including:
         opposing jaw members movably mounted with respect to one another, at least one of the jaw members including a temperature-sensing electrically-conductive tissue-contacting plate, the electrically-conductive tissue-contacting plate including:
            a tissue-contacting surface;
            a bottom surface opposite the tissue-contacting surface;
            a knife channel formed through the tissue-contacting surface and the bottom surface and configured to receive a knife blade for cutting tissue;
            an inner zone defined on the bottom surface and surrounding the knife channel;
            an outer zone defined along the outer periphery of the bottom surface and surrounding the inner zone;

a first passive temperature sensor formed on the bottom surface within the inner zone, the first passive temperature sensor connected to a first conductive trace printed on the bottom surface within the inner zone; and a second passive temperature sensor formed on the bottom surface within the outer zone, the second passive temperature sensor connected to a second conductive trace printed on the bottom surface within the outer zone, wherein the first and second passive temperature sensors are configured to passively sense a tissue temperature and the jaw members are moveable from a first position in spaced relation relative to one another to at least one subsequent position wherein the jaw members cooperate to grasp tissue therebetween;

an electrosurgical power generating source; and a controller in communication with the first and second passive temperature sensors via the respective first and second conductive traces, the controller operably coupled to the electrosurgical power generating source and configured to control at least one operating parameter associated with the electrosurgical power generating source based on one or more signals indicative of a tissue impedance value and indicative of the tissue temperature passively sensed by the first and second passive temperature sensors for regulating thermal spread during use of the end-effector assembly to electrosurgically treat tissue.

2. The electrosurgical system of claim 1, wherein the temperature-sensing electrically-conductive tissue-contacting plate of the at least one of the jaw member is configured to allow selectively adjustable heating of the outer zone and the inner zone.

3. The electrosurgical system of claim 1, wherein the controller is configured to control at least one operating parameter associated with the electrosurgical power generating source based on one or more signals indicative of the sensed tissue temperature in the outer zone and the inner zone.

4. The electrosurgical system of claim 3, wherein the at least one operating parameter of the electrosurgical power generating source is selected from the group consisting of temperature, impedance, power, current, voltage, mode of operation, and duration of application of electrosurgical energy.

5. The electrosurgical system of claim 1, wherein the end-effector assembly includes a fixed jaw member mounted in fixed relation to the shaft and a movable jaw member mounted about a pivot coupled to the stationary jaw member.

6. The electrosurgical system of claim 1, wherein the first and second passive temperature sensors are formed on the bottom surface by vapor deposition, each of the first and second passive temperature sensors being a thermocouple.

7. The electrosurgical system of claim 1, wherein the electrosurgical power generating source is in electrical communication with the housing and configured to deliver electrosurgical power to the end effector assembly through the shaft.

8. A method of controlling vessel sealing, comprising:
providing an electrosurgical instrument having an end-effector assembly including opposing jaw members movably mounted with respect to one another, at least one of the jaw members including a temperature-sensing electrically-conductive tissue-contacting plate having:
a tissue-contacting surface and a bottom surface opposite the tissue-contacting surface;
a knife channel formed through the tissue-contacting surface and the bottom surface and configured to receive a knife blade for cutting tissue;
an inner zone defined on the bottom surface and surrounding the knife channel; and
an outer zone defined along the outer periphery of the bottom surface and surrounding the inner zone;
positioning the jaw members to energize tissue;
transmitting energy from an electrosurgical power generating source to the at least one of the jaw members;
passively sensing a first temperature of the tissue via a first passive temperature sensor formed on the bottom surface within the outer zone and connected to a first conductive trace printed on the bottom surface within the outer zone;
passively sensing a second temperature of the tissue via a second passive temperature sensor formed on the bottom surface within the inner zone and connected to a second conductive trace printed on the bottom surface within the inner zone;
transmitting a first signal indicative of the first temperature to a controller operably associated with the electrosurgical power generating source via the first conductive trace; and
controlling at least one operating parameter associated with the electrosurgical power generating source based on the transmitted first signal indicative of the first temperature of the tissue for regulating thermal spread during the transmitting of energy from the electrosurgical power generating source to the at least one of the jaw members.

9. The method of controlling vessel sealing of claim 8, wherein the at least one operating parameter associated with the electrosurgical power generating source is selected from the group consisting of temperature, impedance, power, current, voltage, mode of operation, and duration of application of electrosurgical energy.

10. The method of controlling vessel sealing of claim 8, wherein transmitting the first signal indicative of the first temperature of the tissue includes measuring a temperature of the tissue using a sensor module coupled to the controller.

11. A method of controlling vessel sealing, comprising:
providing an electrosurgical instrument having an end-effector assembly including opposing jaw members movably mounted with respect to one another, each one of the jaw members including a temperature-sensing electrically-conductive tissue-contacting plate defining having:
a tissue-contacting surface and a bottom surface opposite the tissue-contacting surface;
a knife channel formed through the tissue-contacting surface and the bottom surface and configured to receive a knife blade for cutting tissue;
an inner zone defined on the bottom surface and surrounding the knife channel; and
an outer zone defined along the outer periphery of the bottom surface and surrounding the inner zone;
moving at least one jaw member relative to the other jaw member to grasp tissue between the tissue-contacting surface of each one of the temperature-sensing electrically-conductive tissue-contacting plates;

transmitting energy from an electrosurgical power generating source to at least one of the jaw members;

passively sensing a temperature of the tissue via a first passive temperature sensor formed on the bottom surface within the outer zone;

passively sensing a temperature of the tissue via a second passive temperature sensor formed on the bottom surface within the inner zone; and controlling at least one operating parameter associated with the electrosurgical power generating source based on one or more signals indicative of the temperature of the tissue sensed by the first and second passive temperature sensors for regulating thermal spread during the transmitting of energy from the electrosurgical power generating source to the at least one of the jaw members.

12. The method of controlling vessel sealing of claim 11, wherein the at least one operating parameter associated with the electrosurgical power generating source is selected from the group consisting of temperature, impedance, power, current, voltage, mode of operation, and duration of application of electrosurgical energy.

\* \* \* \* \*